United States Patent [19]

Nanjho et al.

[11] Patent Number: 5,371,557
[45] Date of Patent: Dec. 6, 1994

[54] STEREOSCOPIC RETINAL CAMERA

[75] Inventors: Tsuguo Nanjho, Toyohashi; Nobuyuki Yano, Okazaki; Tokio Ueno, Chiryu, all of Japan

[73] Assignee: Nidek Co., Ltd., Japan

[21] Appl. No.: 947,912

[22] Filed: Sep. 21, 1992

[30] Foreign Application Priority Data

Sep. 30, 1991 [JP] Japan .................. 3-280724
Oct. 31, 1991 [JP] Japan .................. 3-313305

[51] Int. Cl.⁵ .............................................. A61B 3/14
[52] U.S. Cl. ....................... 351/206; 351/211; 351/221
[58] Field of Search ............... 351/201, 206, 208, 211, 351/221

[56] References Cited

U.S. PATENT DOCUMENTS

| | | | |
|---|---|---|---|
| 3,533,342 | 10/1970 | McMillin | 351/206 |
| 4,187,014 | 2/1980 | Kato et al. | 351/206 |
| 4,248,505 | 2/1981 | Muchel et al. | 351/221 |
| 4,283,124 | 8/1981 | Matsumura | 351/206 |
| 4,436,388 | 3/1984 | Takahashi et al. | 351/206 |
| 4,469,416 | 9/1984 | Isono | 351/206 |
| 4,669,837 | 6/1987 | Schirmer et al. | 351/221 |
| 4,699,481 | 10/1987 | Matsumura | 351/206 |
| 4,988,184 | 1/1991 | Akiyama | 351/221 |

FOREIGN PATENT DOCUMENTS

| | | | |
|---|---|---|---|
| 2744707 | 4/1979 | Germany | 351/206 |
| 57-13294 | 3/1982 | Japan | . |
| 61-39050 | 9/1986 | Japan | . |

Primary Examiner—Richard A. Bertsch
Assistant Examiner—Howard R. Richman
Attorney, Agent, or Firm—Parkhurst, Wendel & Rossi

[57] ABSTRACT

A stereoscopic retinal camera comprises an illuminating optical system, a photographing optical system, an observation optical system and a focus detection optical system. The focusing optical system consists of an index projecting system combined with one of the two light paths of the observation optical system, and an index detecting system combined with the other light path of the observation optical system. The respective positions of the focusing lenses of the photographing optical system are adjusted so that a sharp image of the focusing index is detected by the index detecting system. Thus, the stereoscopic retinal camera can be easily focused without requiring any particular skill and is capable of enabling the minute observation of the fundus of the eye by means of a direct-vision viewfinder.

16 Claims, 9 Drawing Sheets 37a  37b 37a  37b

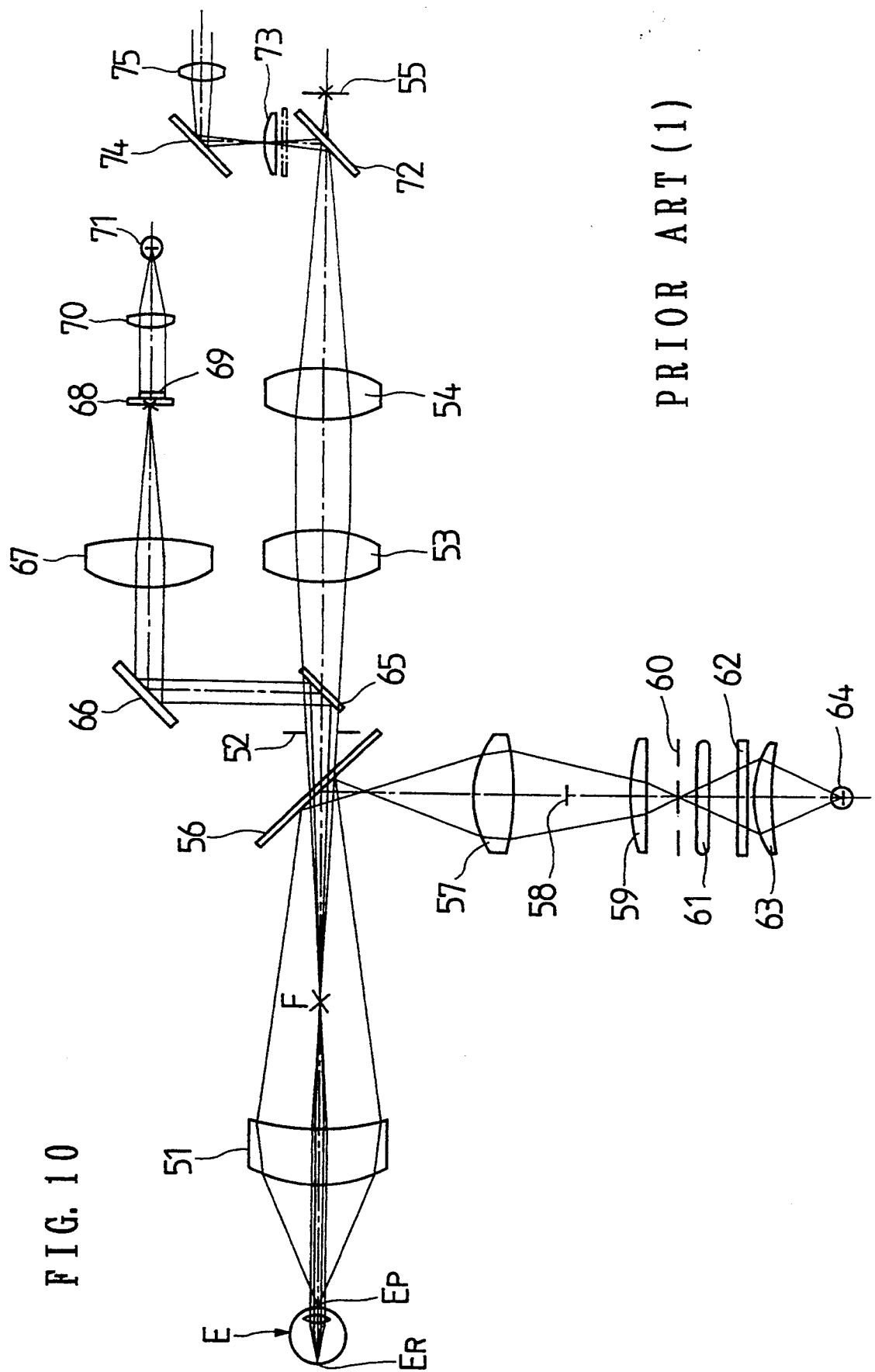
FIG. 10  PRIOR ART (1)

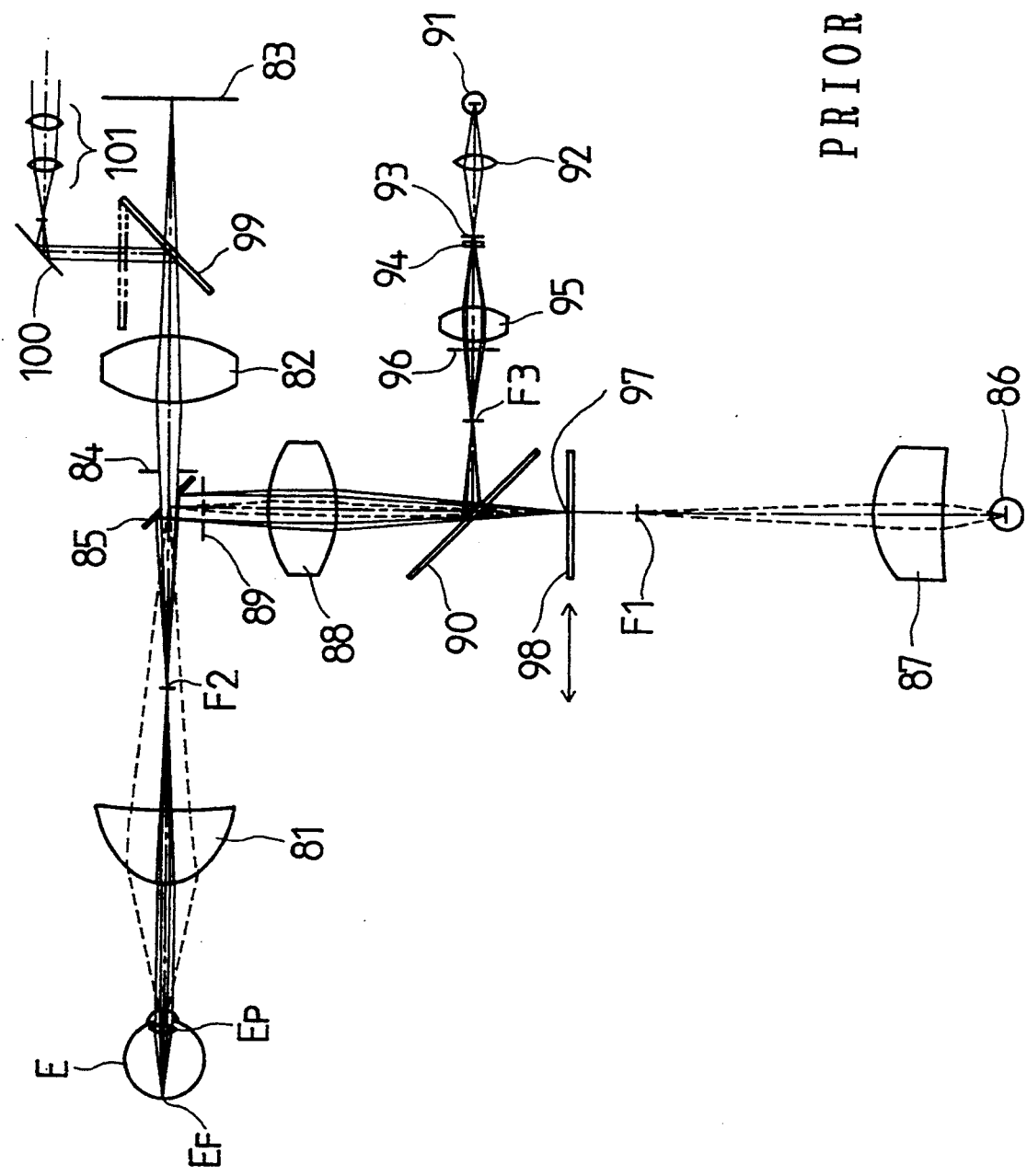
FIG. 11 PRIOR ART (2)

STEREOSCOPIC RETINAL CAMERA

BACKGROUND OF THE INVENTION

1. Field of the Invention

The present invention relates to a stereoscopic retinal camera and, more particularly, to a focus detecting system to be incorporated into a stereoscopic retinal camera.

2. Description of the Prior Art

In focusing a conventional stereoscopic retinal camera on the spatial image of the retina, the spatial image is superposed on the reticule of a viewing system and the focusing condition of the spatial image is observed through the viewing system. Since the condition of the image in the viewfinder is directly dependent on the refracting power of the eyes of the observer, the refracting power of the viewfinder must be exactly adjusted and accurate focusing requires highly skillful focusing technique.

Referring to FIG. 10, a monocular retinal camera disclosed in Japanese Patent Publication (Kokoku) No. Sho 61-39050 comprises: a photographing optical system comprising an objective lens 51 to be disposed opposite to the eye E, a diaphragm 52 in a conjugate relation with the pupil EP of the eye E, a focusing lens 53, an image-forming lens 54 and a film 55 (the focusing lens 53 and the image-forming lens 54 constitute an afocal optical system); a viewfinder optical system comprising a reflecting mirror 72 disposed before the film 55, a field lens 73 disposed on a path along which a light beam reflected by the reflecting mirror 72 passes, a reflecting mirror 74 and an ocular 75; an illuminating optical system comprising a perforated reflecting mirror 56 disposed at a position before the diaphragm 52 on the light path of the photographing optical system, a relay lens 57 disposed on a path along which a light beam reflected by the perforated reflecting mirror 56 passes, a condenser lens 59, a circular slit plate 60, a flash lamp 61 for stroboscopic photography, a heat filter 62, a condenser lens 63 and an illuminating light source 64; and an index projecting system for facilitating focusing, comprising a reflecting mirror 65 disposed at a position after the diaphragm 52 on the light path of the photographing optical system, a reflecting mirror 66, a relay lens 67, a slit index 68, a deflecting prism 69 disposed contiguously with the slit index 68, a condenser lens 70 and a light source 71.

Light beam emitted by the illuminating light source 64 is reflected by the perforated mirror 56 and the reflected light beam passes through the objective lens 51 to illuminate the fundus ER. The light path of the index projecting system is branched from the light path of the photographing optical system by the reflecting mirror 65, i.e., a light path dividing means, disposed behind the perforated mirror 56. Thus, the focusing operation is not effected by illuminating condition, and the index projecting system and the photographing optical system are interlocked simply. Since the index illuminating light beam passes through the space between the illuminating light beam and the photographing light beam or overlap part of the illuminating light beam, the path of the index illuminating light beam needs delicate positional adjustment. The light path dividing means must be positioned so that the light path dividing means may not intercept the light beam of the focusing lens system.

A monocular retinal camera disclosed in Japanese Patent Publication (Kokoku) No. Sho 57-12294 is provided with a direct-vision viewfinder to observe the image of an index formed on the fundus by projecting a plurality of light beams cooperatively forming the image of the index for focusing, i.e., focus detection.

As shown in FIG. 11, the monocular retinal camera has a photographing optical system and an illuminating optical system comprising an objective lens 81, a photographing lens 82 serving also as a relay lens, a film 83, a diaphragm 84, a perforated mirror 85 for reflecting illuminating light, provided with a central hole, an illuminating light source 86, a condenser lens 87, a relay lens 88, and a ring slit 89. A light beam emitted by the illuminating light source 86 is converged on a focal point F1 by the condenser lens 87, gathered on the ring slit 89 by the relay lens 88, reflected by the perforated mirror 85 toward the objective lens 81 and focused on the pupil EP of the eye E by the objective lens 81 to illuminate the fundus EF. The image light reflected by the fundus EF passes through the refraction system of the eye E and the objective lens 81, is focused on the rear focal point F2 of the objective lens 81, passes through the hole of the mirror 85 and the diaphragm 84, and focused on the film 83 by the photographing lens 82 to form the image of the fundus EF on the film 83. The relay lens 88 of the illuminating optical system is equivalent to the photographing lens 82 of the photographing optical system. The relay lens 88 and the photographing lens 82 are equidistant from the perforated mirror 85. A half mirror 90 is disposed on the light path of the illuminating optical system before the relay lens 88, i.e., at a position on the side of the light source 86 with respect to the relay lens 88, so that the image of the index projected by an index projecting system is reflected toward the respective light paths of the illuminating optical system and the photographing optical system so that the image of an index is projected on the fundus EF. The index projecting system comprises a light source 91, a condenser lens 92, a slit index 93 disposed near a position where the condenser lens 92 gathers the light emitted by the light source 91, a split image prism 94 disposed near the slit index 93, a relay lens 95, and a two-hole diaphragm 96. The image of the slit index 93 is formed by the relay lens 95 on a plane FJ, which is in a conjugate relation with the film 83. The position of the two-hole diaphragm 96 corresponds to the position of the image of the ring slit 89 formed by the relay lens 88, the distance between the two holes is equal to the diameter of the image of the ring of the ring slit 89. A transparent glass plate 98 having a shading portion 97 of a size large enough to cover the image of the index formed on the fundus EF and capable of being removably inserted in the light path of the illuminating optical system is disposed at a position in a conjugate relation with the plane F3 to prevent the image of the index formed on the fundus EF being obscured by the illuminating light.

A method of focusing the index projecting system will be described hereinafter. The light image of the index 93 is split into two light images by the split image prism 94. Then, the two light images pass through the two holes of the two-hole diaphragm 96, the lenses 88 and 81, and reach the fundus EF to form the images of the index 93 on the fundus EF. The images formed on the fundus EF is observed through a viewfinder optical system comprising a viewfinder mirror 99 capable of being removably placed in the light path between the photographing lens 82 and the film 83, a reflecting mirror 100 and an ocular 101. Then, the photographing lens 82 and the relay lens 88 are shifted so that the film 83 and the plane F3 are in a conjugate relation with respect to the light reflected by the fundus EF, or the film 83, and the index projecting system including the plane F3 are moved to focus the photographing optical system. However, when this index projecting system is incorporated into a stereoscopic retinal camera, the two images of the index are further split if the convergence of the eyes of the observer is not appropriate, which makes focusing difficult, because two images are observed by the stereoscopic retinal camera. Although it may be possible to observe the fundus stereoscopically for minute inspection by the stereoscopic retinal camera provided with a direct-vision viewfinder, the image of the fundus and that of the index overlap each other and part of the fundus cannot be observed.

SUMMARY OF THE INVENTION

Accordingly, it is an object of the present invention to provide a stereoscopic retinal camera which can be easily focused without requiring any particular skill.

Another object of the present invention is to provide a stereoscopic retinal camera capable of obviating shading the image of the fundus by an index projecting system and of enabling the minute observation of the fundus by means of a direct-vision viewfinder.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the stereoscopic retinal camera of this invention, which enables the stereoscopic observation of the fundus of the eye and capable of photographing the stereoscopic picture of the fundus by dividing a light beam reflected by the fundus into two light beams and transmitting the two light beams respectively along the light paths of separate image forming optical systems, comprises a focusing lens for bringing the fundus of the eye into focus, a focusing index disposed in one of the image forming optical systems in a conjugate relation with the fundus and a photographing plane, and a photodetecting means disposed in the other image forming optical system in a conjugate relation with the photographing plane.

BRIEF DESCRIPTION OF THE DRAWINGS

The above and other objects, features and advantages of the present invention will become more apparent from the following description taken in connection with the accompanying drawings, in which:

FIG. 10 is a diagrammatic top view of the optical systems of a prior art retinal camera; and FIG. 11 is a diagrammatic side view of the optical systems of another prior art retinal camera.

DETAILED DESCRIPTION OF THE PREFERRED EMBODIMENTS

Figure 1:
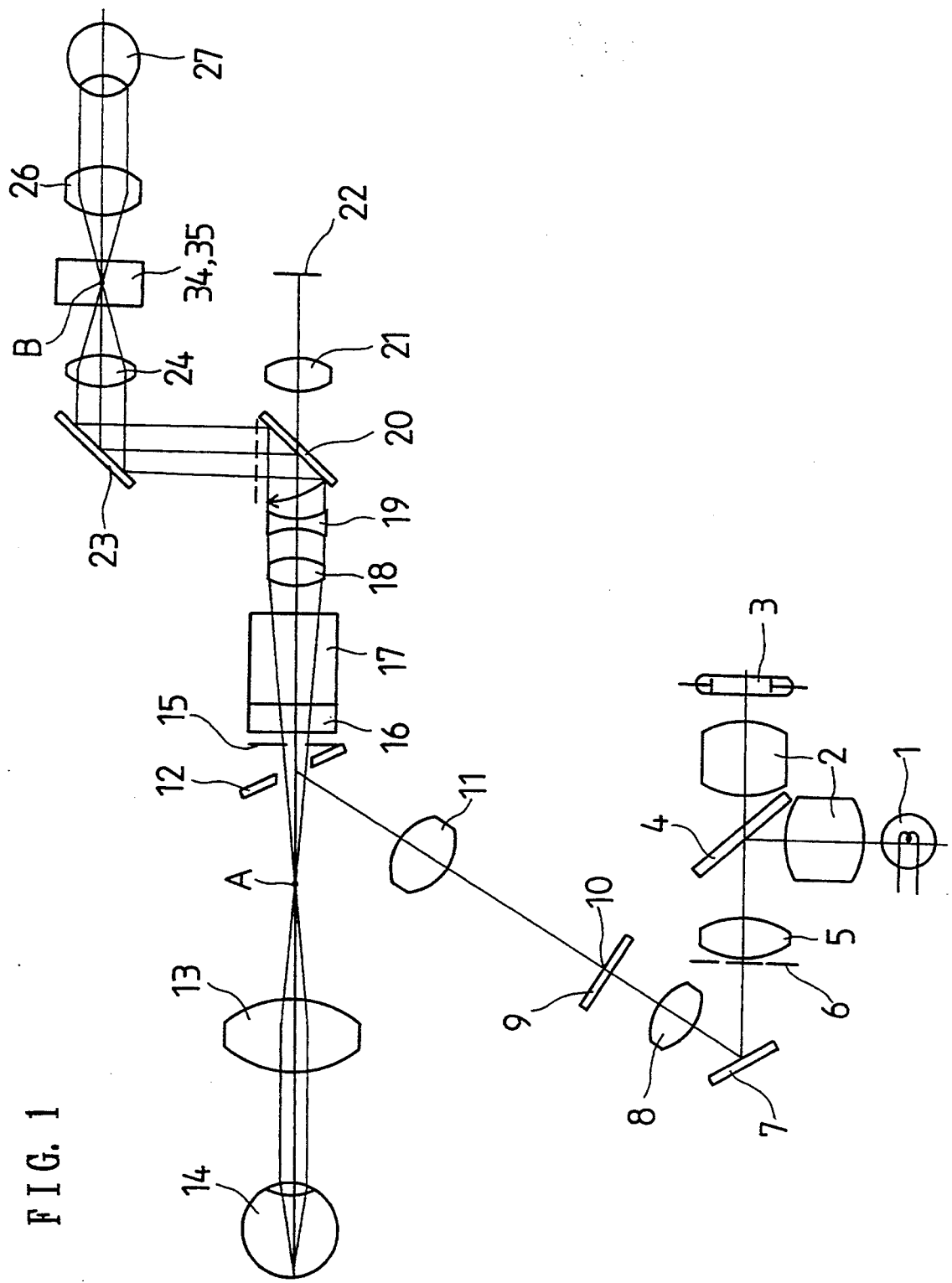
FIG. 1 is a diagrammatic side view of the optical systems of a stereoscopic retinal camera in a first embodiment according to the present invention.
Figure 2:
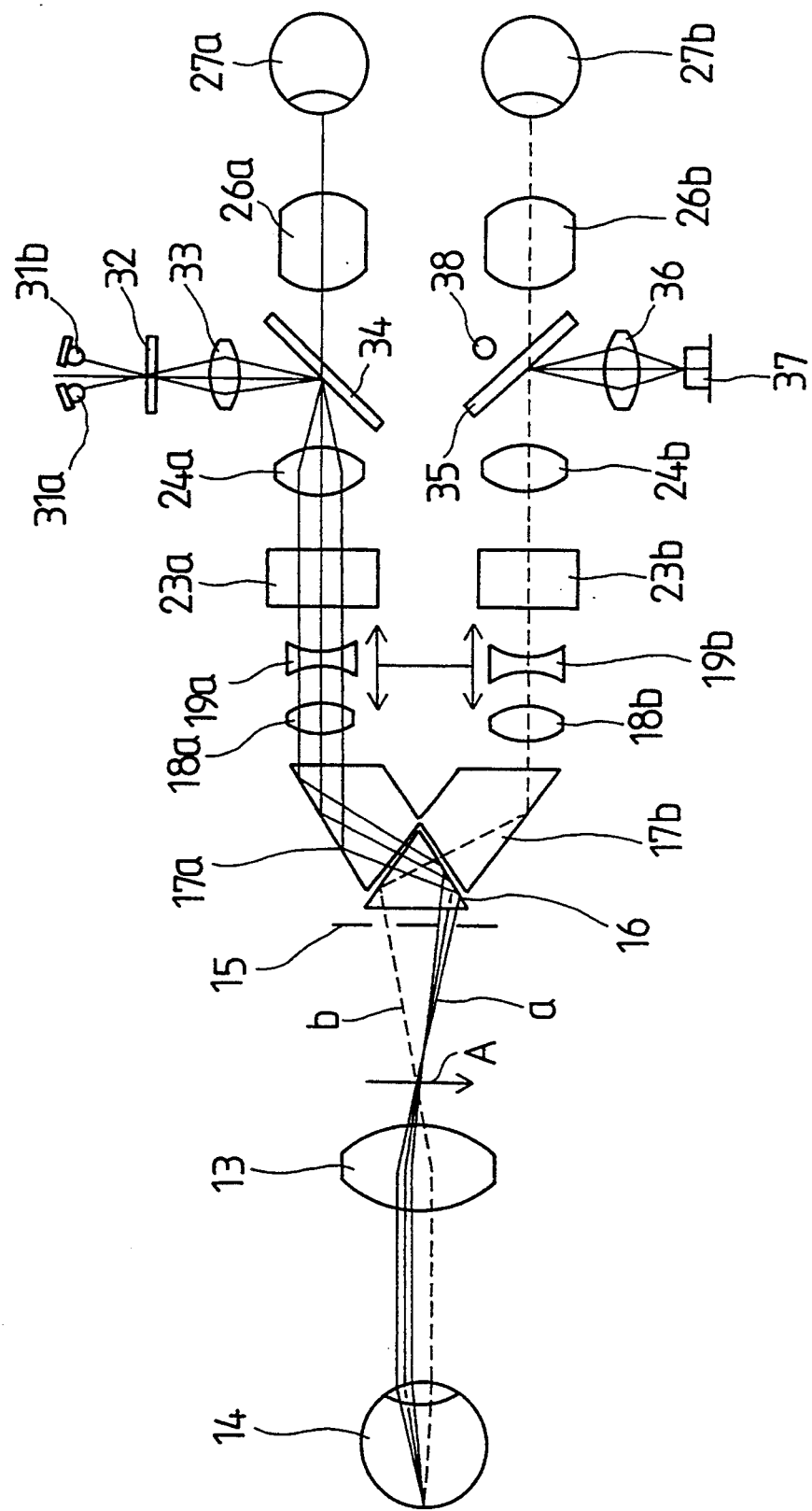
FIG. 2 is a diagrammatic top view of the optical systems of the stereoscopic retinal camera of FIG. 1.

First Embodiment (FIGS. 1 and 2)

A stereoscopic retinal camera in a first embodiment according to the present invention comprises an illuminating optical system, a photographing optical system, an observation optical system and a focus detection optical system.

Illuminating Optical System

The illuminating optical system comprises a halogen lamp 1, i.e., a light source of illumination for observation, condenser lenses 2, a xenon flash lamp 3, i.e., a light source of illumination for photographing, a beam splitter 4, a relay lens 5, an aperture diaphragm 6, a mirror 7 for deflecting a light path, an illuminating relay lens 8, an index plate 9 provided with a central black point 10 for eliminating detrimental light, an illuminating lens 11, a perforated mirror 12 and an objective lens 13. The halogen lamp 1 and the xenon flash lamp 3 are in a conjugate relation with respect to the condenser lenses 2. The aperture diaphragm 6 is provided with a circular slit. An intermediate image of the slit is formed near the opening of the perforated mirror 12, the intermediate image of the slit is reflected by the perforated mirror 12 and the objective lens 13 focuses the image of the slit near the cornea to illuminate the fundus of the eye 14.

Photographing Optical System

A two-hole diaphragm 15 is in a conjugate relation with the pupil of the eye 14 with respect to the objective lens 13. The two-hole diaphragm 15 splits the light beam into two light beams as shown in FIG. 2. Indicated at 16 and 17 are light beam splitting prisms. The light beam splitting prism 17 collimates the two light beams so that the collimated light beams pass along two parallel paths separated from each other by a predetermined distance.

The light beam reflected by the fundus of the eye 14 is focused at a point A in an inverted image by the objective lens 13, passes through the opening of the perforated mirror 12, the two-hole diaphragm 15, the light beam splitting prisms 16 and 17, relay lenses 18

(18a and 18b), focusing lenses 19 (19a and 19b) and image forming lens 21. The image forming lens 21 forms the image of the fundus on the film 22. The focusing lenses 19a and 19b are movable along the optical axis of the photographing optical system. The positions of the focusing lenses 19a and 19b are adjusted according to the refracting power of the eye 14 to focus the image of the fundus on the film 22.

A swing mirror 20 can be turned between a position to reflect the light beam toward the observation optical system and a position to allow the light beam to pass along the optical axis of the photographing optical system to the film 22. In photographing the picture of the fundus, the swing mirror 20 is turned up in the direction of the arrow in synchronism with the flashing action of the xenon flash lamp 3 to allow the light beam reflected by the fundus to fall on the film 22.

Observation Optical System

The observation optical system and the photographing optical system use the objective lens 13, the swing mirror 20 and the components between the objective lens 13 and the swing mirror 13 in common. When observing the fundus, the swing mirror 20 is set on the light path of the photographing optical system to reflect the observation light beam reflected by the fundus and passed through the components from the objective lens 13 through the focusing lenses 19a and 19b toward mirrors 23a and 23b. The observation light beam reflected by the mirrors 23a and 23b passes through observation image forming lenses 24a and 24b, field stops, not shown, and oculars 26a and 26b, and fall on the right eye 27a and the left eye 27b of the observer.

Focusing Optical System

The focusing optical system consists of an index projecting system and an index detecting system. The index projecting system is combined with one of the right and left light paths of the observation optical system (photographing optical system) and the index detecting system is combined with the other light path of the observation optical system (photographing optical system).

The index projecting system has infrared LEDs 31a and 31b, i.e., light sources, which are disposed symmetrically with respect to the optical axis of the index projecting system. Indicated at 32 is an index plate, i.e., a pinhole plate, at 33 is a relay lens and at 34 is a hot mirror, which reflects an infrared beam and transmits a visible light beam.

The index detecting system has a hot mirror 35 having the same spectral characteristics as the hot mirror 34 of the index projecting system has. Indicated at 36 is a relay lens, at 37 is a two-section light receiving element and at 38 is a visible LED which indicates focusing condition represented by the output signal of the two-section light receiving element 37.

The operation of the stereoscopic retinal camera thus constructed will be described hereinafter.

The stereoscopic retinal camera is mounted on a movable table, not shown, which is moved relative to a fixed table by a sliding mechanism. The examinee's head is held on a head support fixed to the fixed table, and the halogen lamp 1 is turned on to illuminate the eye 14. The joystick is operated to align the image of the aperture diaphragm 6 on the cornea with the pupil of the eye 14 so that the fundus is illuminated properly.

The light beam reflected by the fundus is focused to form an inverted image of the fundus at the point A.

The light beam passed the perforated mirror 12 is split into a right light beam and a left light beam by the two-hole diaphragm 15. The light beam splitting prism 16 disposed directly behind the two-hole diaphragm 15 interchanges the right light beam and the left light beam. Then, the light beams are deflected by the prisms 17a and 17b, and the deflected light beams are focused in erect images of the fundus by the pair of image forming lens systems including the relay lenses 18a and 18b, the focusing lenses 19a and 19b, and the observation image forming lenses 24a and 24b on the field stops of the oculars. The observer views the erect images for the stereoscopic observation of the fundus.

The observer turns the focusing knob duping the binocular observation of the images to focus the focusing lenses 19a and 19b and makes the fine adjustment of the alignment of the image of the aperture diaphragm 6 with the pupil of the eye 14 so that flares of the illuminating light will not appear around the right and left images.

The positions of the focusing lenses 19a and 19b are determined by the following procedure using the focusing optical system.

Infrared beams emitted by the infrared LEDs 31a and 31b pass through the pinhole of the index plate 32 and the relay lens 33 and fall on the hot mirror 34. The hot mirror 34 reflects the infrared beam so that the infrared beam passes along the optical axis of the observation optical system. Then, the infrared beam passes along continuous lines as shown in FIG. 2 and is focused in the image of the pinhole of the index plate 32 on the fundus. The infrared image of the pinhole of the index plate 32 illuminated by the infrared beam, reflected by the fundus passes along broken lines shown in FIG. 2 along the light path of the observation optical system and falls on the hot mirror 35. The infrared image reflected by the hot mirror 35 is focused by the relay lens 36 on the two-section light receiving element 37.

Figure 3:
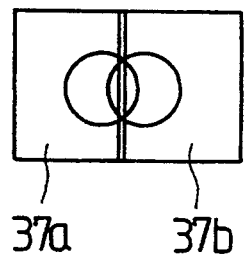
FIGS. 3(a) and 3(b) are a view of an out-of-focus pinhole image formed on a two-section light receiving element and a view of an in-focus pinhole image on the two-section light receiving element, respectively.
Figure 3:
Figure 3:
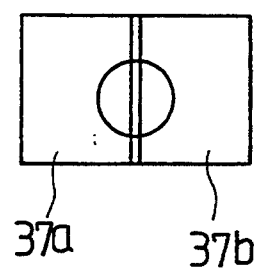

When the respective positions of the focusing lenses 19a and 19b on the corresponding optical axes are adjusted so that the index plate 32 is in a conjugate relation with the fundus, the focusing lenses 19a and 19b are perfectly in focus. If the focusing lenses 19a and 19b are out of focus, the image of the pinhole of the index plate 32 formed on the fundus is blurred and split into two portions and, consequently, two images of the pinhole are formed on the sections 37a and 37b of the two-section light receiving element 37 as shown in FIG. 3(a). Since the sections 37a and 37b of the two-section light receiving element 37 are unbalanced in the quantity of incident light, the focusing lenses 19a and 19b are adjusted so that the two images coincide with each other in a sharp image of the pinhole on the two-section light receiving element 37 as shown in FIG. 3(b). In this state, the two sections 37a and 37b are balanced in the quantity of incident light.

Figure 4:
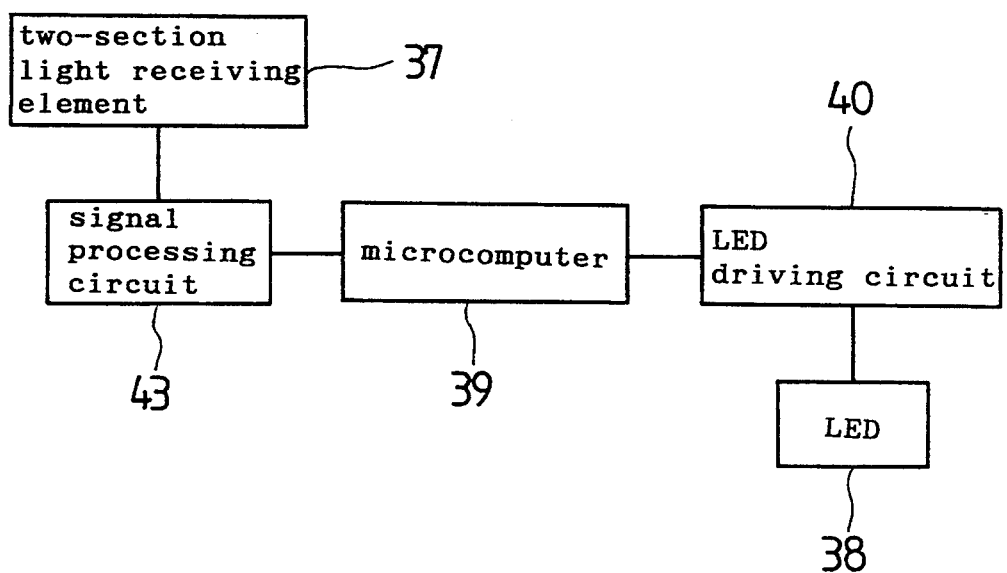
FIG. 4 is a block diagram of assistance in explaining the operation of a control unit included in the stereoscopic retinal camera of FIG. 1 in processing signals provided by a two-section light image receiving element included in the stereoscopic retinal camera of FIG. 1.

Referring to FIG. 4 showing the procedure of a control operation for processing signals provided by the two-section light receiving element 37, a signal processing circuit 43 compares signals provided by the two-section light receiving element 37 and, when the difference between the signals provided respectively by the two sections 37a and 37b of the two-section light receiving element 37 is smaller than a predetermined value, a microcomputer 39 drives a LED driving circuit 40 to turn on the LED 36 provided in the ocular 26b to indicate that the focusing lenses 19a and 19b are in focus.

Figure 5:
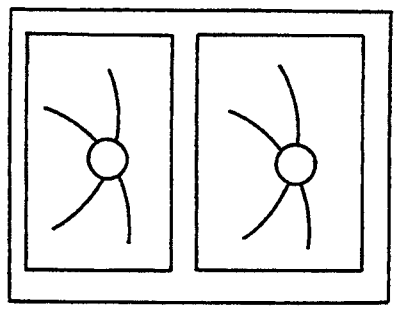
FIG. 5 is a photograph of the fundus taken by the stereoscopic retinal camera of FIG. 1.

After the operations for aligning the image of the aperture diaphragm 6 with the pupil of the eye 14 and for focusing the focusing lenses 19a and 19b have been completed, a shutter release button is depressed. Then, the swing mirror 20 is lifted up and the xenon flash lamp 3 flashes synchronously to form the image of the fundus on the film 22. The automatic operations of the stereoscopic retinal camera are controlled by the microcomputer 39. Thus, a stereoscopic picture of the fundus as shown in FIG. 5 is obtained.

The observation optical system may be combined with a CRT to display the image of the fundus on the CRT.

Since the focusing optical system has the index projecting system and the index detecting system separately, the index detecting system is not effected by light beam reflected within the optical systems of the stereoscopic retinal camera. Since the focusing optical system is combined with the observation optical system and the photographing optical system, the focusing optical system, the observation optical system and the photographing optical system are able to use the focusing lenses in common, and the stereoscopic retinal camera can be highly accurately focused.

Figure 6:
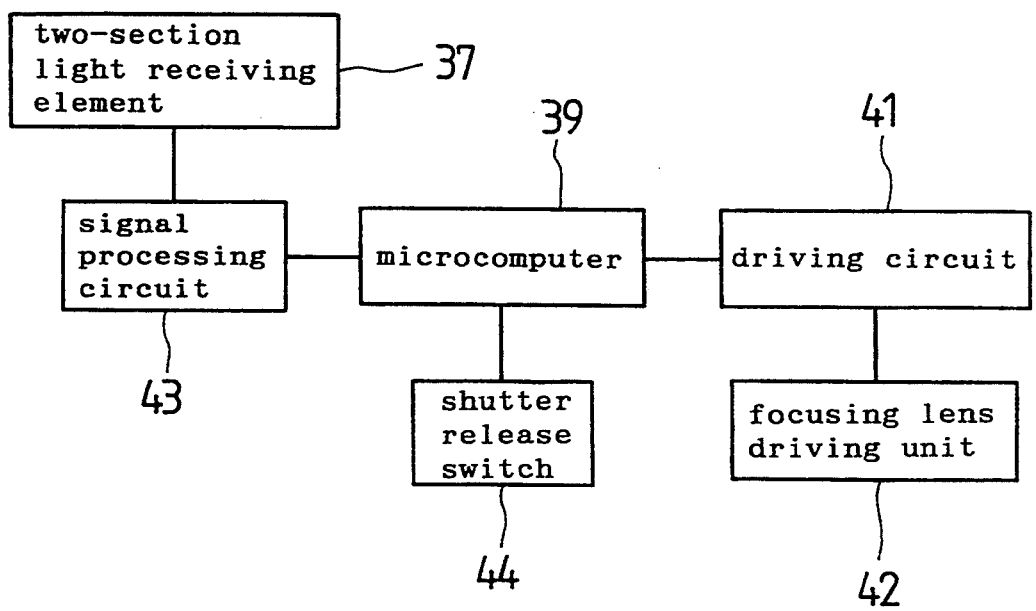
FIG. 6 is a block diagram of a control unit included in a stereoscopic retinal camera in a second embodiment according to the present invention in processing signals provided by a two-section light image receiving element included in the same stereoscopic retinal camera.

Second Embodiment (FIG. 6)

A stereoscopic retinal camera in a second embodiment according to the present invention is similar in construction to the stereoscopic retinal camera in the first embodiment, except that the stereoscopic retinal camera in the second embodiment is provided with a control unit as shown in FIG. 6 which controls the stereoscopic retinal camera for automatic focusing operation.

Referring to FIG. 6, signals provided by the two sections 37a and 37b of the two-section light receiving element 37 are processed by a signal processing circuit 43 and the output signal of the signal processing circuit 43 is applied to a microcomputer 39. Then, the microcomputer 39 controls a focusing lens driving unit 42 through a driving circuit 41 according to the output signal of the signal processing circuit 43 to bring the focusing lenses 19a and 19b into focus. After the focusing lenses 19a and 19b have been focused, the microcomputer 39 turns on a shutter release switch 44 to take the picture of the fundus.

Figure 7:
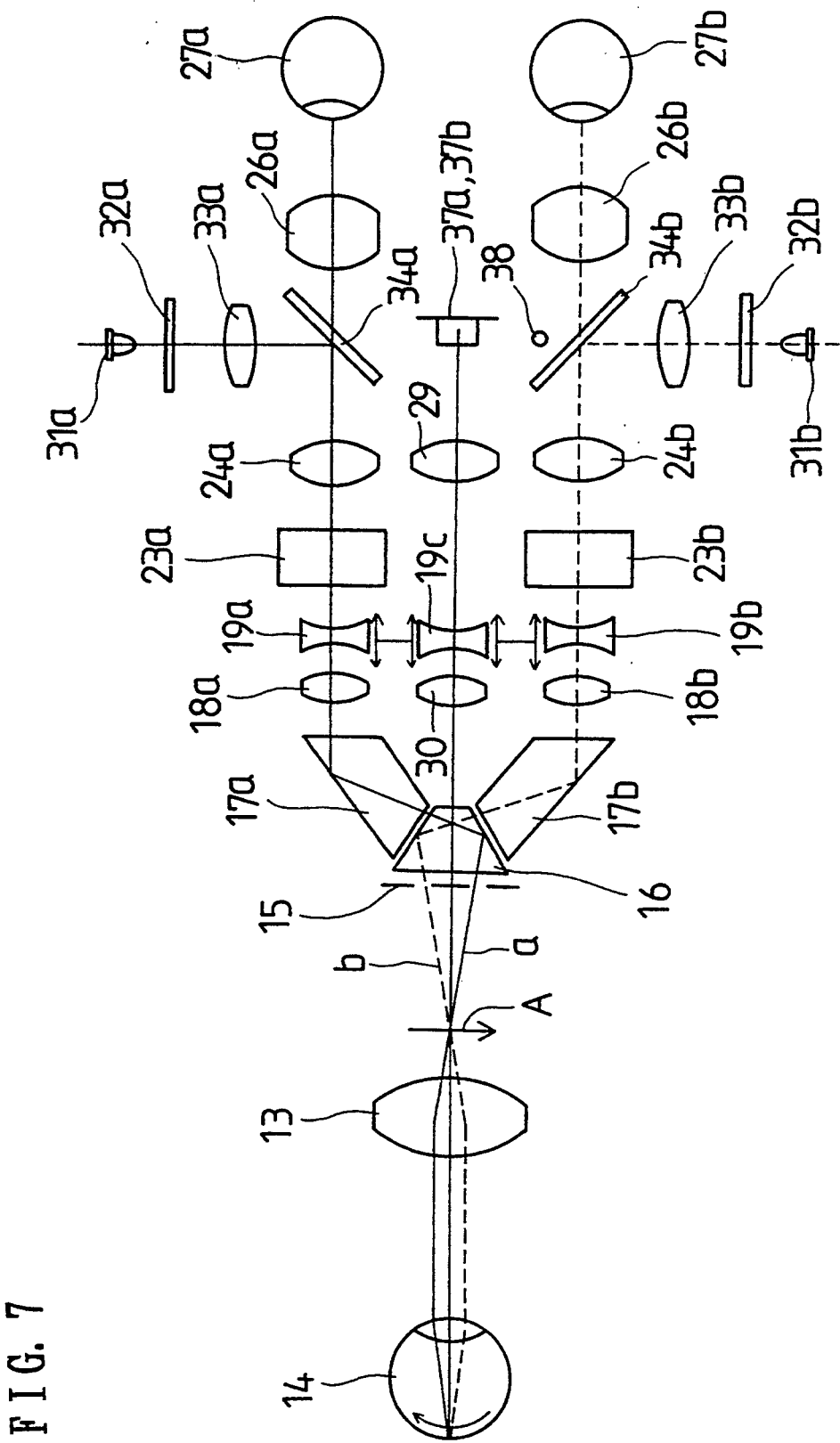
FIG. 7 is a diagrammatic top view of the optical systems of a stereoscopic retinal camera in a third embodiment according to the present invention.

Third Embodiment (FIG. 7)

In the first and second embodiments, the index projecting system of the focusing optical system is combined with either the observation optical system or the photographing optical system, and the index detecting system of the focusing optical system is combined with the other. In the third embodiment, the images of focusing indices are projected through both an observation optical system and a photographing optical system, and the images are detected by a detection optical system disposed on the optical axis of an objective lens.

A stereoscopic retinal camera in the third embodiment will be described with reference to FIG. 7, in which parts like or corresponding to those of the stereoscopic retinal camera in the first embodiment are denoted by the same reference characters and the description thereof will be omitted to avoid duplication.

Focusing Optical System

Referring to FIG. 7, a focusing optical system consists of an index projecting system and an index detecting system.

a. Index Projecting System

The index projecting system is combined with the right and left light paths of the observation/photographing optical system and comprises index illuminating light sources 31a and 31b, index plates 32a and 32b, which are in a conjugate relation with a film 22, relay lenses 33a and 33b through which the images of the pinholes of the index plates 32a and 32b are projected on the fundus of the eye 14, and beam splitters 34a and 34b, which combine the index projecting system with the observation/photographing optical system. The images of the pinholes of the index plates 32a and 32b reflected by the beam splitters 34a and 34b pass through image forming lenses 24a and 24b, focusing lenses 19a and 19b and relay lenses 18a and 18b, which are the components of the observation/photographing optical system, and fall perpendicularly on the flat surfaces of light beam splitting prisms 17a and 17b. The light beam splitting prisms 17a and 17b reflect the images so that the images pass through openings formed in a two-hole diaphragm 15 and an objective lens 13 and fall on the fundus of the eye 14.

b. Index Detecting System

The index detecting system comprises a two-section light receiving element 37 having two sections 37a and 37b, and a visible LED 38 fop indicating focusing condition on the basis of signals provided by the two-section light receiving element 37. The two-section light receiving element 37 is in a conjugate relation with a point B.

The objective lens 13 forms the intermediate images of the pinholes of the index plates 32a and 32b reflected by the fundus and that of the fundus at a point A. Then, the reflected light beam passes through the central opening of the two-hole diaphragm 15, the relay lens 30, a focusing lens 19c and an image forming lens 29, and fall on the sections 37a and 37b of the two-section light receiving element 37 to form the images of the pinholes, i.e., the indices.

The images of the pinholes of the index plates 32a and 32b illuminated by the index illuminating light sources 31a and 31b are projected through the right and left light paths of the observation/photographing optical system on the fundus. The images of the pinholes, i.e., the indices, of the index plates 32a and 32b reflected by the fundus is focused on the sections 37a and 37b of the two-section light receiving element 37 by the index detecting system.

Each of the index plates 32a and 32b may be illuminated by a plurality of light sources. The index illuminating light sources 31a and 31b may be infrared light sources and the light receiving element 37 may be an infrared light receiving element to reduce dazzling effect on the eye. When infrared light sources are used, the images of the pinholes projected on the fundus are invisible, and the invisible images of the pinholes facilitate the observation and photographing of the fundus.

The stereoscopic retinal camera in the third embodiment may be provided with the control unit of the stereoscopic retinal camera in the second embodiment for automatic focusing.

Figure 8:
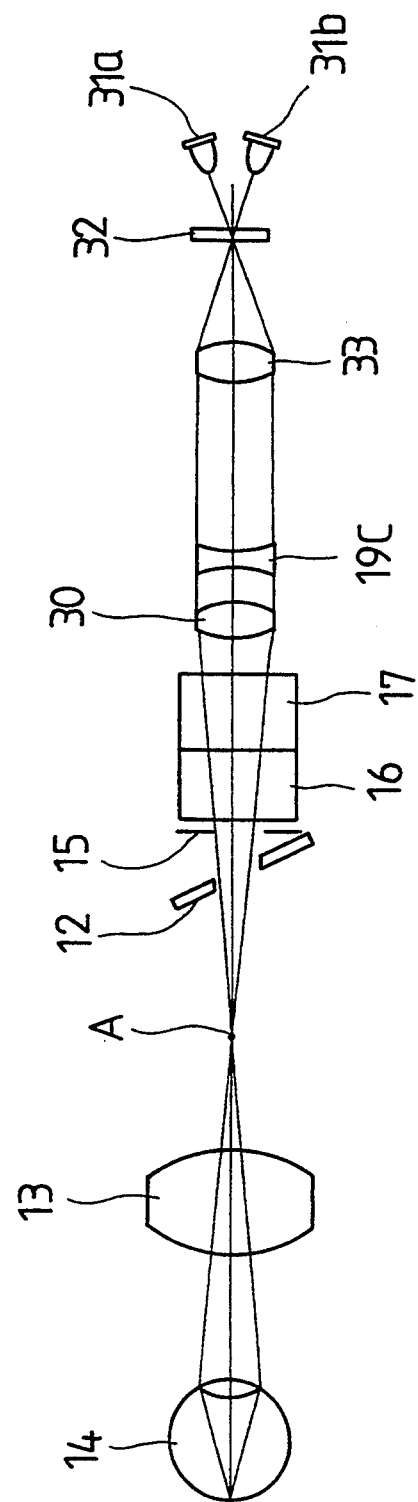
FIG. 8 is a diagrammatic side view of the optical systems of a stereoscopic retinal camera in a fourth embodiment according to the present invention.
Figure 9:
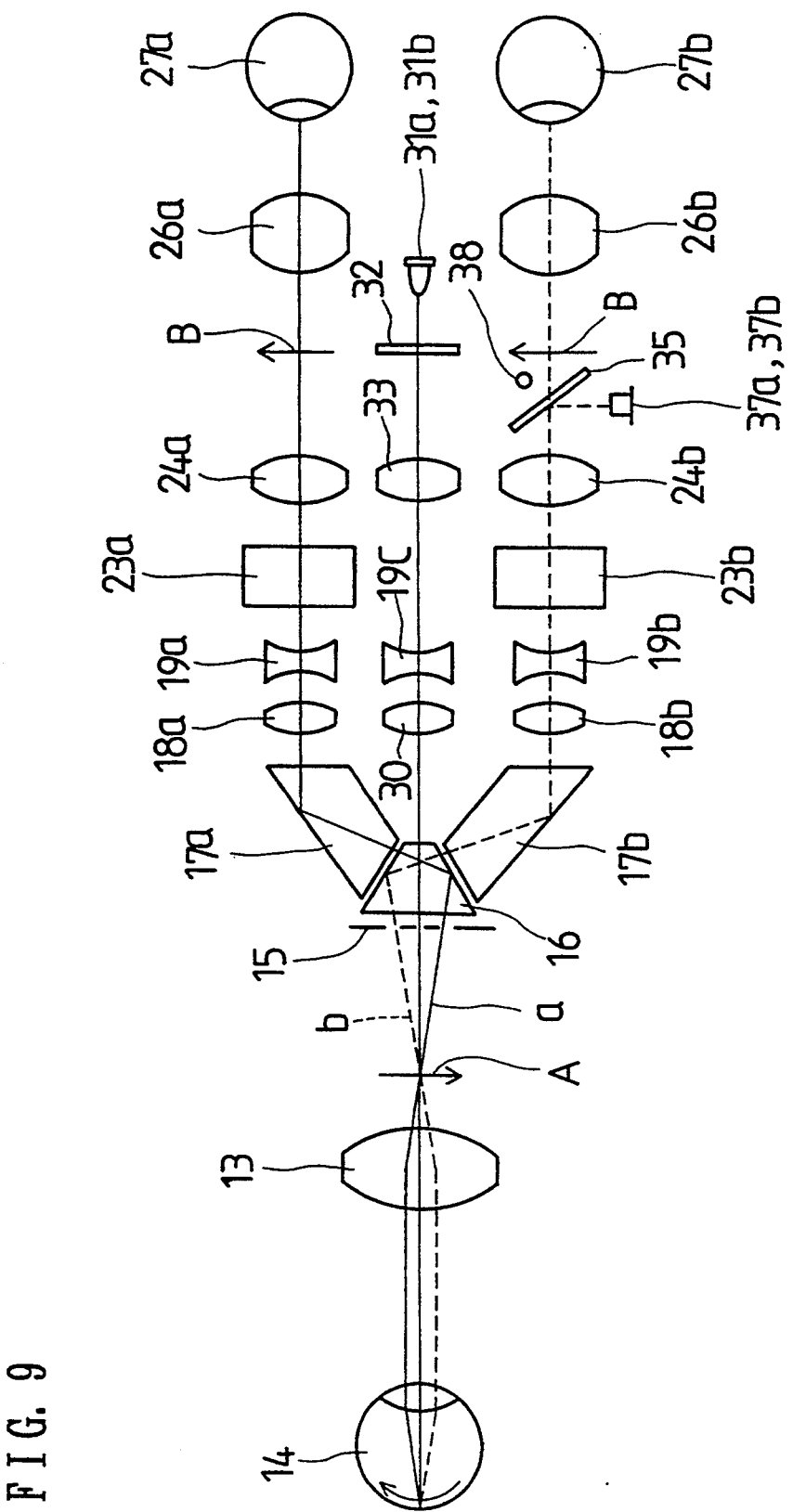
FIG. 9 is a diagrammatic top view of the optical systems of the stereoscopic retinal camera of FIG. 8.

Fourth Embodiment (FIGS. 8 and 9)

A stereoscopic retinal camera in a fourth embodiment according to the present invention, which is similar to the stereoscopic retinal camera in the first embodiment, will be described with reference to FIGS. 8 and 9, in which parts like or corresponding to those of the stereoscopic retinal camera in the first embodiment are denoted by the same reference characters and the description thereof will be omitted.

In the fourth embodiment, an index projecting system is disposed on the optical axis of an objective lens 13, and the image of an index reflected by the fundus is detected by either the right or the left light path of an observation/photographing optical system.

A focusing optical system is disposed between the right and left light paths of the observation/photographing optical system. The focusing optical system comprises an index plate 32 provided with a pinhole, i.e., an index, index illuminating light sources 31a and 31b for illuminating the index plate 32 to project the image of the pinhole, relay lenses 33 and 30 for projecting the image of the index plate 32 on the fundus of the eye 14, and a focusing lens 19c disposed between the relay lenses 33 and 30, and able to move along the optical axis. The index plate 32 is in a conjugate relation with the film 22. The focusing lens 19c is interlocked with the focusing lenses 19a and 19b. The light sources 31a and 31b are arranged one over the other so that the image of the index plate 32 will readily fall on the light beam splitting prism 16. The surfaces of the light beam splitting prism 16, on the optical axis of the index projecting system are perpendicular to the optical axis of the index projecting system.

The image of the index plate 32 falls on the surface of the light beam splitting prism 16 perpendicularly to the same surface, passes through the opening of a two-hole diaphragm 15 and an objective lens 13 and falls on the fundus of the eye 14.

Referring to FIG. 9, the index detecting system of the focusing optical system comprises a beam splitter 35, a two-section light receiving element 37 having sections 37a and 37b, and a visible LED 38 for indicating focusing condition according to signals provided by the sections 37a and 37b of the two-section light receiving element 37. The two-section light receiving element 37 is in a conjugate relation with a point B with respect to the beam splitter 35.

The image forming lenses 24a and 24b of the observation optical system form the images of the index of the index plate 32 reflected by the fundus at the points B. The image of the index formed by the image forming lens 24b and reflected by the beam splitter 35 is formed on the sections 37a and 37b of the two-section light receiving element 37.

The fine adjustment of the alignment of the image of the index with the eye 14 is made so that flares do not appear around the right and left images, and the respective positions of the focusing lenses 19a and 19b are adjusted for accurate focusing.

The image of the index plate 32 illuminated by the index illuminating light sources 31a and 31b is projected on the fundus. The image of the index reflected by the fundus is formed at the point B by the observation optical system and is reflected on the light receiving element 37 by the beam splitter 35. Since the focusing lens 19c moves together with the focusing lenses 19a and 19b, the focusing lens 19c is focused accurately when the index plate 32 is in a conjugate relation with the fundus. If the focusing lens 19c is out of focus, split images of the index are formed on the fundus and split images are formed on the light receiving element 37 as shown in FIG. 3(a). In such a state, the respective output signals of the sections 37a and 37b of the light receiving element 37 are unbalanced. Then, the position of the focusing lens 19c is adjusted for accurate focusing, in which a sharp image of the index is formed on the light receiving element 37.

In the foregoing embodiments, the position of the index plate 32 may be adjusted instead of the position of the focusing lens 19c for focusing.

Although the invention has been described in its preferred embodiments with a certain degree of particularity, obviously many changes and variations are possible therein. It is therefore to be understood that the present invention may be practiced otherwise than as specifically described herein without departing from the scope and spirit thereof.

What is claimed is:

1. A stereoscopic retinal camera comprising:
   an illuminating optical system for illuminating a fundus of an eye;
   an observation/photographing optical system comprising a two-hole diaphragm and a light beam splitting means;
   an index projecting system for projecting an image of a focusing index through a central portion of the two-hole diaphragm on to the fundus; and
   a photodetecting means for detecting the image of the focusing index reflected by the fundus, wherein said photodetecting means is disposed in said observation/photographing optical system;
   wherein said index projecting system includes an element, said element comprising at least one of a movable lens and a movable index, movable along an optical axis of the index projecting system, and said observation/photographing optical system includes focusing lenses that are moved according to the movement of the element of the index projecting system.

2. A stereoscopic retinal camera according to claim 1, wherein the focusing lenses of said observation/photographing optical system are interlocked mechanically with the element of said index projecting system.

3. A stereoscopic retinal camera according to claim 1, wherein the focusing lenses of said observation/photographing optical system are moved by at least one of manual operation and automatic operation according to the movement of the element of said index projecting system.

4. A stereoscopic retinal camera comprising:
   an illuminating optical system comprising a first optical path for illuminating a fundus of an eye;
   an observation/photographing optical system comprising a second optical path separate from said first optical path and including a two-hole diaphragm and a light beam splitting means;
   an index projecting system for projecting an image of a focusing index through the light beam splitting means of the observation/photographing optical system in the second optical path on to the fundus; and
   an index detecting system for detecting the image of the focusing index formed on the fundus through a central portion of the two-hole diaphragm in the second optical path.

5. A stereoscopic retinal camera according to claim 4, wherein said index projecting system projects images of the focusing index through reflecting mirrors disposed respectively on a pair light of paths of said observation/photographing optical system.

6. A stereoscopic retinal camera according to claim 4, wherein an element is included in said index detecting system, said element comprising at least one of a photodetecting means and a movable lens, that is interlocked with focusing lenses of said observation/photographing optical system, and position of the element is adjusted according to a result of a detection of the image of the focusing index by the index detecting system.

7. A stereoscopic retinal camera comprising:
an illuminating optical system comprising a first optical path for illuminating a fundus of an eye;
an observation/photographing optical system comprising a second optical path separate from the first optical path and including a two-hole diaphragm and a light beam splitting means;
an index projecting system for projecting an image of a focusing index in the second optical path through a central portion of the two-hole diaphragm on to the fundus; and
a photodetecting means for detecting the image of the focusing index reflected by the fundus in the second optical path, wherein said photodetecting means is disposed in said observation/photographing optical system.

8. A stereoscopic retinal camera according to claim 7, wherein said photodetecting means is disposed on a branch light path formed by a beam splitter included in said observation/photographing optical system.

9. A stereoscopic retinal camera according to claim 7 further comprising a driving means for driving at least one of a movable lens and a movable index plate, and focusing lenses, included in the observation/photographing optical system according to a focusing condition detected by said photodetecting means.

10. A stereoscopic retinal camera which enables the stereoscopic observation of a fundus of an eye and is capable of photographing a stereoscopic picture of the fundus by dividing a light beam reflected by the fundus into two light beams and transmitting the two light beams respectively along light paths of separate first and second image forming optical systems, said stereoscopic retinal camera comprising:
focusing lenses located in the first and second image forming optical systems for bringing the fundus of the eye into focus at a photographic plane;
an index projecting system, for projecting a focusing index onto the fundus of the eye, disposed in the first image forming optical system in a conjugate relation with the fundus and a photographing plane; and
an index detecting system, including a photodetecting means, disposed in the second image forming optical system, for detecting the focusing index projected on the fundus.

11. (Amended) A stereoscopic retinal camera according to claim 10, wherein the focusing index projected by the index projecting system is an infrared spot.

12. A stereoscopic retina camera according to claim 11, wherein the index projecting system includes a plate having a pinhole located therein, and a plurality of light sources disposed symmetrically with respect to an optical axis of the index projecting system.

13. A stereoscopic retinal camera according to claim 1, wherein
the index projecting system includes an index plate disposed out of an optical path of the first image forming optical system, an infrared light source to illuminate the index plate, and a mirror disposed on the optical path to reflect an infrared light emitted from the infrared light source, and
the index detecting system includes a mirror disposed in the second image forming optical system to reflect the infrared light, and a light detecting system to receive the infrared light beam reflected by the mirror.

14. A stereoscopic retinal camera according to claim 1, wherein a focusing condition of said focusing index detected by said photodetecting means is indicated by an indicating means.

15. A stereoscopic retinal camera according to claim 14, wherein said indicating means is disposed within a field of observation.

16. A stereoscopic retinal camera according to claim 1, wherein said focusing lenses are driven by a driving means according to a focusing condition of said focusing index detected by said photodetecting means.

* * * * *